United States Patent [19]

Byrne et al.

[11] Patent Number: 5,352,192
[45] Date of Patent: Oct. 4, 1994

[54] MEDICAL DEVICE

[75] Inventors: Philip O. Byrne, Newcastle upon Tyne; Thomas S. J. Elliot, Sutton Coldfield, both of England

[73] Assignee: British Technology Group Limited, London, England

[21] Appl. No.: 869,608

[22] Filed: Apr. 16, 1992

[30] Foreign Application Priority Data

Apr. 27, 1991 [GB] United Kingdom ............ 9109166.0

[51] Int. Cl.$^5$ ............................................. A61N 1/30
[52] U.S. Cl. ............................ 604/20; 604/21; 604/49
[58] Field of Search ................. 128/798, 802, 803; 604/19, 20, 21, 49

[56] References Cited

U.S. PATENT DOCUMENTS

| | | | |
|---|---|---|---|
| 600,290 | 3/1898 | Muir | 604/20 |
| 743,306 | 11/1903 | Merwin | 604/20 |
| 791,730 | 6/1905 | Stanger | 604/20 |
| 1,652,327 | 12/1927 | Richter | 604/21 |
| 2,121,875 | 6/1938 | Kruse et al. | 128/362 |
| 2,482,507 | 9/1949 | Rentschler et al. | 128/419 R |
| 3,491,756 | 1/1970 | Bentov | 128/221 |
| 4,411,648 | 10/1983 | Davis et al. | 604/21 |
| 4,569,673 | 2/1986 | Tesi | 604/20 |
| 4,776,349 | 10/1988 | Nashef et al. | 604/21 |
| 5,154,165 | 10/1992 | Elliott et al. | 604/20 |
| 5,188,738 | 2/1993 | Kaali et al. | 604/4 |

FOREIGN PATENT DOCUMENTS

| | | |
|---|---|---|
| 290811A5 | 6/1991 | Fed. Rep. of Germany . |
| 322202 | 11/1971 | U.S.S.R. .......... 604/20 |
| 0825095 | 4/1981 | U.S.S.R. .......... 604/20 |
| 1005797 | 3/1983 | U.S.S.R. .......... 604/20 |
| 1064956 | 1/1984 | U.S.S.R. .......... 604/20 |
| 2219510A | 12/1989 | United Kingdom . |

OTHER PUBLICATIONS

Abstract SU 995745, Soviet Inventions Illustrated, Jan. 18, 1984, p. 3.
Abstract SU 676917, Soviet Inventions Illustrated, May 14, 1980, p. 12.

Primary Examiner—C. Fred Rosenbaum
Assistant Examiner—Michael Rafa
Attorney, Agent, or Firm—Nixon & Vanderhye

[57] ABSTRACT

A medical device for invasive positioning in the body comprises a liquid flow passage extending between an entry orifice (24) for admitting liquid into the device and an exit orifice from which liquid may pass from the device into the body, and means for establishing a positive electric field at a point (28) within the device. Negatively-charged bacteria are attracted by the positive field towards that point and away from the operative end of the device.

7 Claims, 1 Drawing Sheet

MEDICAL DEVICE

The present invention is a medical device of the type which is used for invasive positioning in the body.

BACKGROUND OF THE INVENTION

It has been observed that infection arising from the presence of invasive and/or implanted medical devices in the human body can be ascribed to at least two distinct sources. Firstly, bacteria may pass from the skin down the outside of the medical device, for example a catheter or cannula. However, there is a second source of potential infection and that is via the interior of the medical device itself. For example, poor clinical technique may allow contamination to occur at a point in the equipment remote from the position of entry of the device to the body and a subsequent liquid flow in the device, such as an injection, can transfer the bacteria into the body.

It is an object of the present invention to provide a novel medical device, wherein this second potential source of infection is combatted by providing a positive electrical field remote from the operative end of the device, preferably out of the liquid flow path through the device. Under normal physiological conditions, the bacteria associated with mammals carry a net negative charge and are therefore attracted by said positive electrical field, away from the operative end of the device.

SUMMARY OF THE INVENTION

The medical device according to the present invention for invasive positioning in the body comprises a liquid flow passage extending between an entry orifice for the admission of liquid into the device and an exit orifice from which liquid may pass from the device into the body, and means for establishing a positive electric field at a point within the device. Very preferably, that point is located further from the exit orifice than is the entry orifice, and preferably out of the line of the liquid flow through the device.

Advantageously, a chamber to receive one or more anti-bacterial agents is disposed at that point.

The means required by the present invention for establishing an electric field may take the form of a pair of electrodes between which a small current, for example between 1 and 10 microamps, may be arranged to flow. As an alternative, an electret material having a persistent positive charge may provide the required field in appropriate circumstances.

BRIEF DESCRIPTION OF THE DRAWINGS

The invention will now be further described with reference to the accompanying drawing, which illustrates, by way of example only and in a schematic illustration, partly in section, a device including a catheter according to the present invention.

DETAILED DESCRIPTION OF THE INVENTION

Figure 1:
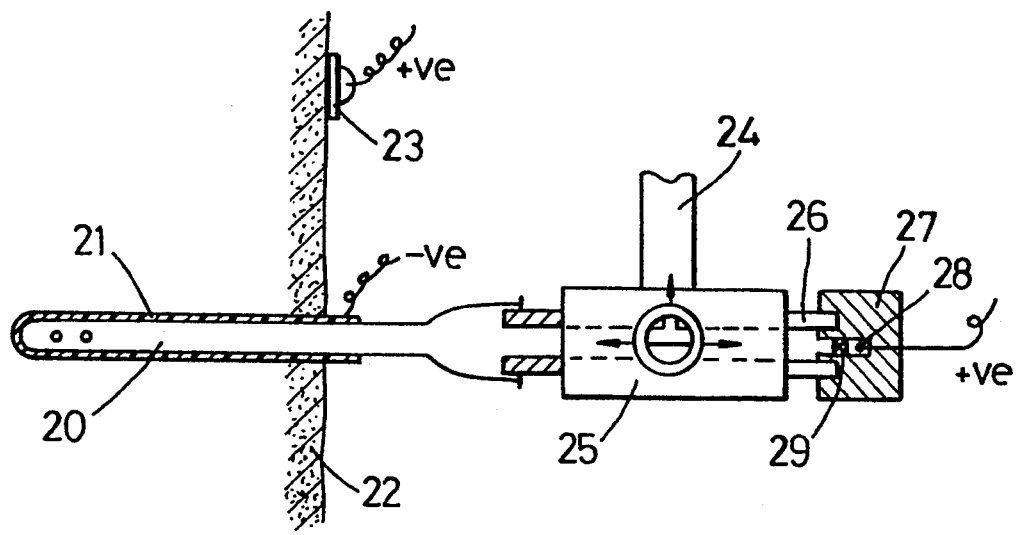

The illustrated catheter 20 has an electrically conductive plastic coating 21 and is shown inserted into the skin 22 of a patient. An electric field is established between the coating 21, acting as a negative electrode, and a skin electrode 23 forming the positive electrode. By means of that field, bacterial attachment to the external surface of the catheter (in the form of the coating 21) is inhibited.

Liquid to be injected into the patient via the catheter 20 is supplied by a line 24 feeding a three-way valve 25. A branch outlet 26 from the valve 25 is closed off by a cap 27, which carries a positively-charged electrode 28 and may itself be made of an electrically conductive plastic or the like. In a chamber in the cap 27 adjacent to the electrode 28 a small plug 29 of a drug-absorbent material is disposed.

In use of the illustrated catheter to provide a continuous or intermittent introduction of a therapeutic drug to a patient, the drug, in liquid form, flows from the line 24 through the valve 25 to the catheter 20. Bacteria arising from contamination in the region of the valve 25 are drawn by the electrode 28 into the cap 27 and are there destroyed by means of an anti-bacterial agent absorbed on the plug 29.

We claim:

1. A medical device for invasive positioning within a body, said device comprising
   an inlet orifice for the admission of liquid into the device;
   an exit orifice for passing liquid from the device into the body;
   a liquid flow passage extending between said inlet orifice and said exit orifice; and
   means for establishing a positive electric field at a point within the device which is out of line of liquid flow from said inlet orifice to said outlet orifice but is in liquid communication with said liquid flow passage, whereby negatively-charged bacteria are attracted away from said passage and towards said point.

2. A medical device according to claim 1, and further comprising a three-way valve disposed between said inlet orifice and said outlet orifice, said valve being connected to provide liquid communication between said inlet orifice, said outlet orifice and said point.

3. A medical device according to claim 1, and further comprising a chamber disposed at said point for receiving at least one anti-bacterial agent.

4. A medical device according to claim 1, wherein said means for establishing a positive electric field comprises a pair of electrodes.

5. A medical device according to claim 1, wherein said means for establishing a positive electric field comprises an electret material having a persistent positive charge.

6. A catheter for invasive positioning in a human body, said catheter comprising:
   an inlet orifice for admission of liquid into the catheter;
   an exit orifice for passage of liquid from the catheter into the body;
   a liquid flow passage extending from said inlet orifice to said exit orifice;
   a negatively-charged electrode surrounding said exit orifice;
   a positively-charged electrode located within said catheter at a position which is in communication with said liquid flow passage and is further from said exit orifice that is said inlet orifice; and
   a chamber for containing anti-bacterial agent, said positively-charged electrode being disposed within said chamber.

7. A method of combatting bacterial infection arising during the administration of a liquid to a patient through a medical device which is a catheter, cannula or the like, said method comprising the steps of:

providing a positive electric field at a point within said medical device which is out of the line of but in communication with the liquid flow through said device, thereby attracting negatively-charged bacteria to said point, and disposing an anti-bacterial agent at said point, thereby destroying said negatively-charged bacteria attracted to said point.

* * * * *